United States Patent [19]

Grossi et al.

[11] Patent Number: 4,919,131
[45] Date of Patent: Apr. 24, 1990

[54] RESECTOSCOPE WITH IMPROVED GUIDE BLOCK AND ELECTRICAL PLUG CONNECTION

[75] Inventors: Benedetto Grossi, Stamford; Thomas W. Bracci, Norwalk, both of Conn.

[73] Assignee: Circon Corporation, Santa Barbara, Calif.

[21] Appl. No.: 202,154

[22] Filed: Jun. 2, 1988

[51] Int. Cl.⁵ ............................................. A61B 17/36
[52] U.S. Cl. .................................................... 606/46
[58] Field of Search ...................... 128/303.13–303.17

[56] References Cited

U.S. PATENT DOCUMENTS

| | | |
|---|---|---|
| D. 251,608 | 4/1979 | Cawood, Jr. et al. . |
| D. 251,609 | 4/1979 | Cawood, Jr. et al. . |
| 2,090,923 | 8/1937 | Wappler .......................... 128/303.15 |
| 2,249,894 | 7/1941 | Goldenstein ..................... 128/303.13 |
| 2,487,502 | 11/1949 | Willinsky ....................... 128/303.14 |
| 2,545,865 | 3/1951 | Wallace ........................... 128/303.15 |
| 3,847,153 | 11/1974 | Weissman ....................... 128/303.14 |
| 3,850,162 | 11/1974 | Iglesias . |
| 4,132,227 | 1/1979 | Ibe . |
| 4,149,538 | 4/1979 | Mrava et al. . |
| 4,326,530 | 4/1982 | Fleury ............................. 128/303.14 |
| 4,538,610 | 9/1985 | Kubota . |
| 4,726,370 | 2/1988 | Karasawa et al. . |
| 4,732,149 | 3/1988 | Stutter ............................. 128/303.17 |

FOREIGN PATENT DOCUMENTS 1548389 12/1968 France .

OTHER PUBLICATIONS

The New Continuous Flow Resectoscope from American ACMI, May 1984.
"ACMI Continuous Flow Resectoscope", Jan. 1987.
"Operating and Maintenance Manual Continuous Flow Resectoscope", American ACMI, Apr. 1983.
"ACMI Adult Resectoscope Operating & Maintenance Manual", American ACMI, June 1984.
"ACMI Adult Resectoscope Operating and Maintenance Manual", American ACMI, June 1984.

Primary Examiner—Max Hindenburg
Attorney, Agent, or Firm—Perman & Green

[57] ABSTRACT

A disconnectable electrical plug for use with a urological endoscope comprising a housing; a conductor; a connector; and an extension block keyed for insertion into a guide block of the endoscope. The extension blocks extends from the housing at a substantially right angle to the entry of the conductor into the housing and is insertable into the guide block in either a first or second position. A urological endoscope is provided comprising a guide block with an electrical plug channel with a first entry on a first lateral side and a second entry on a second lateral side such that an electrical plug can be connected directly to an electrode by mounting the plug in the channel in either the first or second side of the guide block.

4 Claims, 1 Drawing Sheet

U.S. Patent  Apr. 24, 1990  4,919,131
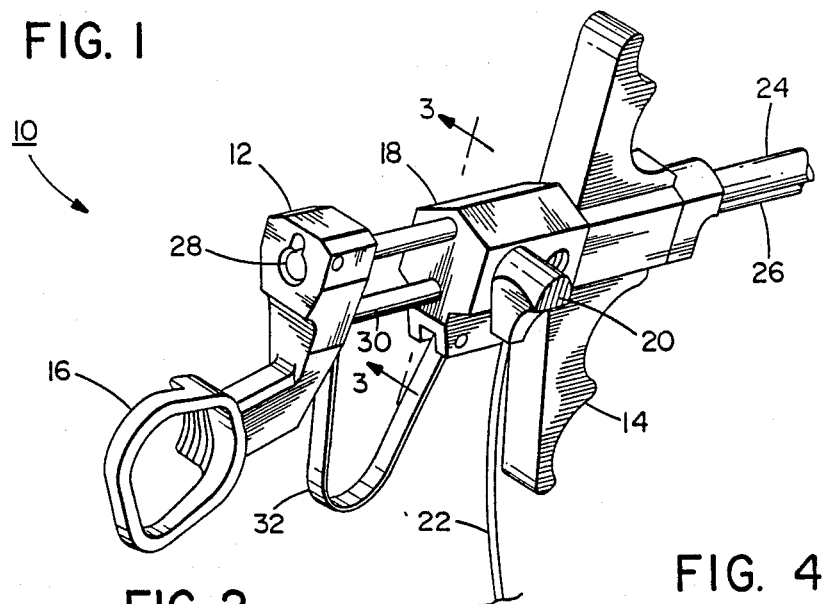
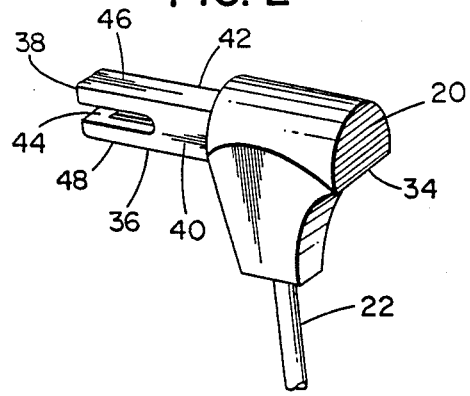
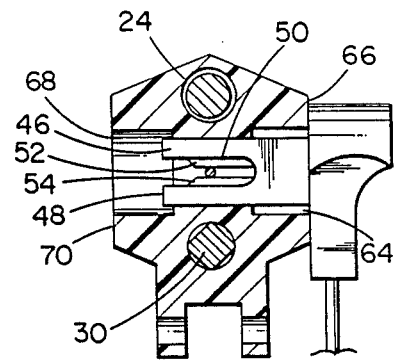
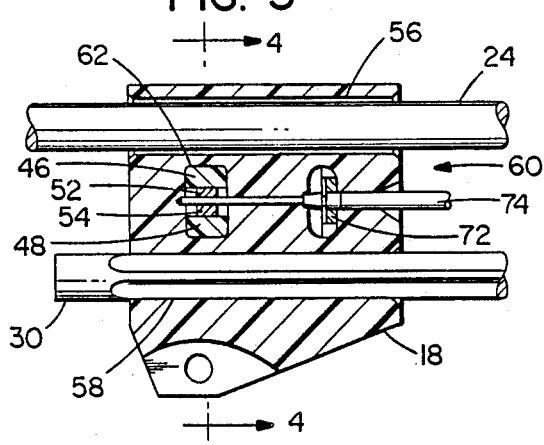
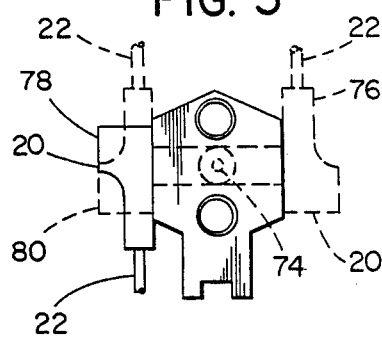

RESECTOSCOPE WITH IMPROVED GUIDE BLOCK AND ELECTRICAL PLUG CONNECTION

BACKGROUND OF THE INVENTION

1. Field of the Invention

This invention relates to medical endoscopes and, more particularly, to a resectoscope with an improved guide block and electrical plug connection.

2. Prior Art

Generally, resectoscopes comprise a hollow sheath, a working element, a telescope and an electrode. The working element generally has a guide block that can slide or move, such as by a rack and pinion mechanism or spring, to move the electrode relative to the telescope. The guide block generally has a hole or connector for receiving a portion of the electrode and another hole for receiving an electric plug. The electric plug supplies electricity to the electrode for resection or the like.

U.S. Pat. No. 4,538,610 to Kubota shows one type of guide block or movable member and an extending connecting part. U.S. Pat. No. 4,149,538 shows a slide portion with a receptacle or channel for receiving the plug of an electrical lead (not shown). However, problems exist with devices in the prior art.

During an operation on a patient, the doctor or operator must feel confident and secure with his instrument. In the past, various different manufactures of medical instruments produced different designs of instruments having electric cords connected at various different locations on their individual instruments. Doctors who were educated or trained on a certain type of instrument feel uncomfortable in changing to other types or makes of the same instrument merely because of the change in orientation of the electrical wire such as in a resectoscope. Hence, a user who is comfortable with a resectoscope such as shown in U.S. Pat. No. 4,538,610, with a connector on the top of the resectoscope, would feel uncomfortable using the resectoscope shown in U.S. Pat. No. 4,149,538, merely because the electric wire for the resectoscope extends downward rather than upward. In addition, the resectoscope shown in U.S. Pat. No. 4,149,538 would probably be uncomfortable for a left handed doctor. This lack of confidence and thus increase the risk to a patient from such increased time.

It is therefore an objective of the present invention to provide a disconnectable electric plug for use with a medical endoscope that can be oriented in different orientations to accommodate different operators.

It is a further objective of the present invention to provide a resectoscope that can accept an electrical plug in several different orientations including on different sides of the resectoscope.

SUMMARY OF THE INVENTION

The foregoing problems are overcome and other advantages are provided by a medical endoscope with an improved electrical plug receptacle and electrical plug connector.

In one embodiment of the invention, a disconnectable electrical plug is provided comprising housing means; conductor means; keying means; and connector means. The keying means comprises an extension block insertable into a guide block of the endoscope. The extension block extends from the housing means at a substantially right angle to an entry of the conductor means into the housing means. The extension block is insertable into the guide block in a first position with the conductor means being in a substantially upwardly extending position or a second position with the conductor means being in a substantially downwardly extending position. The extension block has a receptacle means with the connector means being proximate the receptacle means such that the connector means can contact an electrode.

In accordance with another embodiment of the invention, a urological endoscope is provided comprising frame means and guide block means. The guide block means comprises an electrical plug channel having a first entry on a first lateral side and a second entry on a second lateral side of the guide block. The channel extends through the guide block means between the two entries and intersects an electrode channel such that an electrical plug can be directly connected to an electrode by mounting the plug on either the first or second side of the block to accommodate either a left or right handed operator.

In accordance with another embodiment of the invention, a urological endoscope is provided comprising frame means; guide block means; an electrical connector; and means for limiting insertion of the connector into an electrical plug channel of the guide block means. The guide block means has an electrical plug channel with a first entry on a first side of the guide block means and a second entry on a second side of the guide block means. The electrical connector is insertable into either the first or second entry. The means for limiting insertion of the connector in the socket limits insertion to at least one orientation on each of the sides.

BRIEF DESCRIPTION OF THE DRAWINGS

The foregoing aspects and other features of the invention are explained in the following description, taken in connection with the accompanying drawings wherein:

FIG. 1 is a perspective view of the handle section of a working element of a resectoscope incorporating features of the invention.

FIG. 2 is a perspective view of the electrical plug shown in FIG. 1

FIG. 3 is a cross-sectional side view of the guide block of FIG. 1 taken along lines 3—3.

FIG. 4 is a cross-sectional view of the guide block of FIG. 1 taken along lines 4—4 of FIG. 3.

FIG. 5 is a diagrammatical view of the guide block of FIG. 1 with the electrical plug in different orientations.

DETAILED DESCRIPTION OF THE INVENTION

Referring to FIG. 1, there is shown a partial perspective view of the handle section of a resectoscope working element 10. Although the present invention will be described with reference to the working element 10 of FIG. 1, is should be understood that the present invention can be used with various different types of resectoscope working elements, including Iglesias type working elements and McCarthy type working elements, and can also be employed in any type of medical endoscope using an electrode. In addition, it should be understood that the elements of the present invention can have any suitable size, shape or type of material. Cross-reference is hereby made to the following copending patent applications: "System For Disconnectably Mounting An Endoscope Sheath With An Endoscope Tool" by Grossi et al, Ser. No. 07/202,152, filed June 2, 1988;

"Improved Resectoscope Electrode And Method For Making The same" by Grossi et al., Ser. No. 07/202,153, filed June 2, 1988; "System For Reducing Drag On The Movement Of An Electrode In A Resectoscope And Method Of Making The Same" by Grossi et al., Ser. No. 07/201,667, filed June 2, 1988; Design For A "Resectoscope Electrode", by Grossi et al, Ser. No. 07/203,022, filed June 2, 1988; Design For A "Resectoscope Handle And Latch" by Grossi et al, Ser. No. 07/203,021, filed June 2, 1988; and Design For A "Resectoscope Sheath Latch Receptacle" by O'Hare et al., Ser. No. 07/201,711, filed June 2, 1988 assigned to the same assignee as herein and which was incorporated by reference in their entirety herein.

The working element 10 shown in FIG. 1 is generally known as a Baumrucker type working element. The handle section of the working element generally comprises a frame 12, a handle 14, a thumb guide 16, a guide block 18, and an electrical plug 20 with a conductor 22. The working element 10 also comprises a telescope sheath 24 and an electrode assembly sheath 26 that are insertable into a cooperating sheath (not shown). A telescope (not shown) may be inserted into an aperture 28 in the frame 12 which communicates with the telescope sheath 24 whereby the telescope can be inserted and retained in the telescope sheath 24. The frame 12 also comprises, in this embodiment, a guide bar 30. The guide block 18 and handle 14, in this embodiment, are slidingly mounted on a portion of the telescope sheath 24 and the guide bar 30. A spring 32 biases the handle 14 and guide block 18 in a first forward direction. An operator, having his thumb in the thumb guide 16 and fingers on the handle 14 can move the handle 14 and guide block 18 in a rearward direction compressing the spring 32 and axially moving an electrode assembly 74 which is connected to the guide block 18. The electrical plug 20 is connected inside the guide block 18 directly to a proximal region of the electrode assembly 74 such that electrosurgical current from an electrosurgical generator (not shown) can be transmitted via the conductor 22 and plug 20 directly to the electrode assembly to perform a desired operation.

Referring now to FIG. 2 there is shown a perspective view of the electrical plug 20. The plug 20 generally comprises a housing 34 and an extension block 36. In a preferred embodiment the housing 34 and extension block 36 are comprised of a dielectric material and are molded as a single unit. The housing 34, in this embodiment, is provided with a suitable shape such that an operator can readily grasp the housing for insertion or removal of the plug 20 from the guide block 18. The conductor 22 is generally comprised of a center electrically conductive material such as copper or other suitable material and an outer protective covering of an insulative material. The extension block 36 can generally be described as having a rectangular profile. However, the present invention may have the extension block with any suitable shape. The extension block 36 has a leading face 38 having a slot 44 which extends into the extension block 36 between a first side 40 and a second side 42. The slot 44 is generally centrally located relative to the leading face 38 and generally forms a top arm 46 and a bottom arm 48 in the extension block 36. Mounted in the extension block 36 proximate the slot 44 is an electrical contact or connector 50 having a top portion 52 and a bottom portion 54. The electrical connector 50 is connected to the conductor 22 in the housing 34.

Referring now to FIGS. 3 and 4, a cross sectional side view of the guide block 18 of FIG. 1 is shown taken along lines 3—3 and a cross sectional view of the guide block of FIG. 3 is shown taken along lines 4—4, respectively. The guide block 18, in this embodiment, generally comprises a telescope sheath aperture 56, a guide bar aperture 58, and an electrode assembly proximal end aperture 60 and a plug receptacle or channel 62 having a first entry 64 on a first lateral side 66 of the guide block and a second entry 68 on a second lateral side 70 of the guide block. Suitable means 72 for retaining the proximal end of the electrode assembly 74 are also provided with the guide block 18. The receptacle or channel 62 generally extends entirely through the guide block 18 between the first entry 64 and second entry 68. In the embodiment shown, the receptacle or channel 62 generally intersects the electrode assembly proximal end aperture 60 at a substantially perpendicular angle. The shape of the receptacle or channel 62, as can best be seen in FIG. 3, is generally rectangular such that the extension block 36 of the plug 20 can be matingly receiving therein. In a preferred embodiment the guide block 18 is made of a suitable material such as Teflon, a trademark of E. I. Dupont Co., which has high lubricity, low moisture absorption and a good dielectric strength. Alternatively, the extension block 36 may be slightly tapered to provide easy insertion into the receptacle or channel 62 but nonetheless form a tight fit therewith. As shown in this embodiment, the proximal end of the electrode assembly 74 generally passes through the slot 44 of the extension block 36 with the slot 44 being relatively centrally located relative thereto. The top portion 52 and bottom portion 54 of the contact 50 make an electrical contact with the electrode assembly 74 such that electrosurgical current can be transmitted thereto.

The present invention generally provides for attaching the plug 20 to the guide block 18 at various different orientations and positions, but which nonetheless allow for an electrical contact with the electrode assembly 74. In particular, for the embodiment shown in FIG. 1, the plug 20 can be connected to the electrode assembly 74 on either the first lateral side 66 or the second lateral side 70 of the guide block. In addition, the embodiment shown in FIG. 1 allows for the plug 20 to be orientated in two orientations on each side. FIG. 4 generally illustrates a first position of the plus 20 on the first side 66. As shown, the extension block 36 extends from the housing 34 at a substantially right angle to the entry of the conductor 22 into the housing 34. At this first position the conductor 22 extends from the plug 20 in a substantially downwardly extending orientation.

Referring now to FIG. 5, profile 76 generally illustrates a second position that the plug 20 could have relative to the guide block 18. In this second position the conductor 22 extends away from the housing 34 in a substantially upwardly extending position. Profile 78 generally shows the plug 20 in a third position. This third position generally consists of the plug 20 being mounted to the guide block 18 on the second side 70 with the conductor 22 being oriented in a downwardly extending position. Profile 80 generally illustrates the plug 20 being in a forth position relative to the guide block 18. In this fourth position the plug 20 is connected to the guide block 18 on the second side 70 with the conductor 22 being orientated in a generally upwardly extending position. It is important to note that no matter which position or orientation an operator may choose to connect the plug 20 to the guide block 18, the connector 50 will always make an electrical contact with the electrode assembly 74. In the embodiments shown, this feature is provided by the located slot 44 being positioned in the receptacle or channel 62 at generally the same position at every orientation of the plug 20.

For the embodiment shown and described above, the extension block 36 and at least a portion of the receptacle or channel 62 have been provided with a generally rectangular profile. The feature of the rectangular profile, in this embodiment, limits the number of orientations which the plug 20 can be connected to the guide block 18. For this embodiment, the rectangular profile limits the number of orientations to four; two on each side. However, in alternate embodiments the shape of the extension block and/or receptacle or channel 62 and/or an additional limiting means can be used to limit the orientations of the plug 20 to two; one on each side. Alternatively, any number or orientations can be provided on each side. However, by providing both a first entry 64 on a first lateral side 66 and a second lateral entry 68 on a second lateral side 70 the present invention allows for the electrical plug 20 to be reoriented to accommodate different operators. For example, a right handed operator would generally prefer to have the plug 20 on the first side 66 such that the plug 20 would not interfere with the operator's movement of the guide block 18 or unnecessarily hinder the operators quick and unencombered access to the working element with his left hand. Oppositely, a left handed operator would prefer to have the plug 20 on the second side 70 of the guide block 18 such that he could operate the working element 10 without being annoyed or hindered by the plug 20. In addition, because the plug 20 can be orientated with the conductor 22 extending either in an upwardly extending position or a downwardly extending position, this allows the operator to orientate the conductor 22 as he desires. For instance, many operators prefer to have the conductor 22 extend in an upwardly extending position wherein he could clamp the conductor overhead and would not feel comfortable or confident about the working element unless the conductor was so arranged. Oppositely, there are some operators who do not like the conductor to be extending overhead. They prefer instead to have the conductor extend downwardly to the floor and would not feel comfortable or confident about the working element unless the conductor was so arranged. Thus, the need arose for a working element that could have an electrical plug suitable for both right handed and left handed operators and which could nonetheless be orientated in either an upwardly or downwardly extending position. The present invention provides a solution to this problem.

In addition to the plug being insertable into either a first side 66 or second side 70, for a McCarthy type working element which has a rack and pinion means for moving the guide block and to thus moving the electrode assembly, the guide block may be provided with a pinion channel having a first entry on the first side 66 of the guide block and a second entry on the second side 70 of the guide block. The pinion can be provided such that it is removable from the pinion channel and can be inserted into either the first lateral side or the second lateral side to accommodate either a right handed user or a left handed user.

It should be understood that the foregoing description is only illustrative of the invention. Various alternatives and modifications can be devised by those skilled in the art without departing from the invention. Accordingly, the present invention is intended to embrace all such alternatives, modifications and variances which fall within the scope of the appended claims.

What is claimed is:

1. A urological endoscope comprising:
   frame means; and
   guide block means, said guide block means being movably mounted on said frame means and comprising at least one guide bar channel, an electrode proximal end channel and an electrical plug channel, said electrical plug channel having a first entry on a first lateral side and a second entry on a second lateral side, said electrical plug channel extending through said guide block means between said entries and intersecting said electrode channel, said guide block means further comprising means for limiting insertion of an electrical plug into said electrical plug channel to at least two orientations on each of said sides whereby an electrical plug can be directly connected to an electrode by mounting the plug in said electrical plug channel on either said first or second side of said block to accommodate either a left or right handed operator an in at least either a first or second orientation on either of said first or second sides for allowing an operator to configure the connection of a plug to said guide block means for allowing an operator to feel comfortable and confident with the endoscope.

2. An endoscope as in claim 1 wherein said electrical plug channel intersects said electrode channel at a substantially perpendicular angle.

3. An endoscope as in claim 1 wherein said electrical plug channel is shaped to receive a plug in only two different orientations on each of said first or second sides.

4. An endoscope as in claim 3 wherein said electrical plug channel is generally rectangular in shape.

* * * * *